(12) United States Patent
Pentafragas

(10) Patent No.: US 8,286,631 B2
(45) Date of Patent: Oct. 16, 2012

(54) DRY POWDER INHALATION DEVICE FOR THE SIMULTANEOUS ADMINISTRATION OF MORE THAN ONE MEDICAMENT

(76) Inventor: Dimitrios Pentafragas, Pikermi (GR)

( * ) Notice: Subject to any disclaimer, the term of this patent is extended or adjusted under 35 U.S.C. 154(b) by 958 days.

(21) Appl. No.: 12/295,945

(22) PCT Filed: May 9, 2007

(86) PCT No.: PCT/GR2007/000026
§ 371 (c)(1),
(2), (4) Date: Oct. 3, 2008

(87) PCT Pub. No.: WO2007/129127
PCT Pub. Date: Nov. 15, 2007

(65) Prior Publication Data
US 2009/0250056 A1    Oct. 8, 2009

(30) Foreign Application Priority Data
May 9, 2006 (GR) .................................. 060100275

(51) Int. Cl.
*A61M 11/00* (2006.01)

(52) U.S. Cl. .............................. 128/203.15; 128/203.21

(58) Field of Classification Search ............. 128/200.23, 128/203.15, 203.19, 203.21; 206/528, 532, 206/531, 536, 358, 540, 828; 222/81–83
See application file for complete search history.

(56) References Cited

U.S. PATENT DOCUMENTS

| | | | |
|---|---|---|---|
| 7,318,435 B2 * | 1/2008 | Pentafragas | 128/203.21 |
| 7,931,022 B2 * | 4/2011 | Johnson et al. | 128/203.15 |
| 7,950,389 B2 * | 5/2011 | Eason et al. | 128/203.12 |
| 2007/0062525 A1 * | 3/2007 | Bonney et al. | 128/203.21 |

FOREIGN PATENT DOCUMENTS

| | | |
|---|---|---|
| WO | 98/34663 | 8/1998 |
| WO | 03/061744 | 7/2003 |
| WO | 03/082389 | 10/2003 |
| WO | 2005/076872 | 8/2005 |

* cited by examiner

*Primary Examiner* — Steven Douglas
(74) *Attorney, Agent, or Firm* — Ladas + Parry LLP

(57) ABSTRACT

The present invention relates to a dry powder inhalation device which is suitable for the simultaneous administration of a combination of pharmaceutical ingredients, wherein each pharmaceutical ingredient is packed in a separate blister of the same single dose blister strip. The medicaments that form the combination come into contact just before their exit from the mouthpiece of the device.

13 Claims, 4 Drawing Sheets

DRY POWDER INHALATION DEVICE FOR THE SIMULTANEOUS ADMINISTRATION OF MORE THAN ONE MEDICAMENT

TECHNICAL FIELD

The present invention relates to a dry powder inhalation device suitable for the simultaneous administration of a combination of different medicaments, wherein each medicament is packed in a separate blister of a single dose blister strip.

BACKGROUND OF THE INVENTION

The administration of medicaments by inhalation is one of the most promising approaches in therapy that can be applied to a wide variety of diseases. The first inhaled medicaments were used for the treatment of diseases affecting the airways; however there has been an increased interest recently for the development of inhaled forms of medicaments that target various other diseases, such as diabetes.

The administration of medicaments by inhalation is carried out by using inhalation devices (inhalers). A large number of such devices are comprised in the state of the art. A large category of inhalers includes those wherein the medicament is situated in a receptacle in the form of dry powder and wherein the patient, by using the power of his/hers lungs, creates a streaming of air which carries along the powder which is subsequently inhaled through a mouthpiece. These devices are known as dry powder inhalers (DPIs). The powder in said devices is either situated in a container from where the required amount is measured using an internal mechanism, or it is packed as individual doses in the corresponding receptacles such as blister packs or capsules. The powder comprises the active ingredient which in most cases is combined with one or more excipients.

It is also known from the state of the art that some diseases are treated by a combination of more that one inhaled medicaments which, when this is possible, are preferably administered simultaneously. The simultaneous administration through the inhalation route is preferred over the sequential administration because in this way the patient receives the required dose of the medicaments by inhaling only once and therefore the treatment is achieved by the use of a single inhaler, something which solves many practical problems and results in better compliance by the patient. Furthermore in some cases the simultaneous administration may be proved to be therapeutically more effective comparing to the sequential administration. In the cases of simultaneous administration of a mixture of medicaments the inhalers are the same with the ones used for the administration of a single medicament, the only difference being that this time the pharmaceutical composition comprises the mixture of the active ingredients in the appropriate ratio which in the majority of cases is mixed with one or more excipients.

However, the presence of a mixture of active ingredients in the pharmaceutical composition creates considerable problems. First of all it is possible that an interaction between the active ingredients comprised in the mixture may occur, which may result in their decomposition. This outcome in the best of cases leads to the decreased effectiveness of the treatment as a result of the presence of smaller amounts of the active ingredients in each dose, whereas in the worst cases it may become hazardous for the patient since the decomposition products could not only be therapeutically ineffective but pose a danger to the patient's health. Furthermore, the presence of a mixture of active ingredients creates problems with the development of the appropriate pharmaceutical composition, since each active ingredient has its own physical and chemical characteristics which are not necessarily compatible with the corresponding characteristics of the other ingredient. Consequently, the development of a pharmaceutical composition which is suitable for both ingredients of the mixture becomes more difficult.

One of the dry powder inhalers comprised in the state of the art is that disclosed in WO03082389. Said document discloses a dry powder inhalation device wherein the medicament is packed in the blister of a specially designed single dose blister strip. The device comprises a mouthpiece, a blister strip support surface and a strip storage compartment. The support surface comprises an attachment point (e.g. a protrusion), a cavity which receives the blister of the strip and guides for the correct placement of the strip. The three parts are movably joined to each other. When the blister strip is placed on the support surface and the mouthpiece is in its basic position, the base of the mouthpiece touches the strip and covers completely the powder containing blister.

The mouthpiece of said device comprises three parts, an exterior part and two interior parts of conical shape. The first of the interior parts, whose lower side has two openings and touches the blister of the strip, is divided into two chambers through which the air which enters the mouthpiece carries the powder. Then, the mixture of air and powder passes through the second interior part of the mouthpiece and exits the device.

In order to use said device for the simultaneous administration of a combination of medicaments, the single dose blister strips should contain the mixture of said compounds, with all the aforementioned problems and disadvantages.

The present invention enables the user to inhale simultaneously a combination of two medicaments, while it provides solutions to all of the above-mentioned problems.

DESCRIPTION OF THE INVENTION

The present invention provides a dry powder inhaler which is suitable for the simultaneous administration of more than one medicament. What is meant by the term simultaneous administration is that the patient receives the required dose of the medicaments by inhaling only once. According to the present invention each pharmaceutical ingredient is packed in a separate blister of the same single dose blister strip, wherein the term single dose blister strip designates a strip that contains a single dose of each medicament. The device comprises a mouthpiece, a blister strip support surface and a blister strip compartment. The support surface comprises a point for the attachment of the strip (attachment point), two cavities which receive the blisters of the powder containing strip and guides for the firm placement and the correct alignment of the strip. Preferably the attachment point is a protrusion. The mouthpiece is movably joined to the support surface so as when the device is ready for inhalation the base of the mouthpiece touches the strip and covers completely the powder containing blisters. According to the present invention the administered medicaments come into contact with each other for the first time just before they exit the mouthpiece of the device, as it is explained herein below.

The present invention also provides a blister strip for the storage of a single dose of a combination of medicaments, wherein said strip is comprised of a base sheet and a cover sheet which are made of materials known from the state of the art, such as aluminium, polyamide, paper, polyester etc. The base sheet comprises an attachment formation and two cavities, each of them comprising a different pharmaceutical ingredient. The attachment formation is preferably a hole.

The base sheet is sealed in the area around the cavities by a cover sheet whose free end, while initially covering the attachment formation, is folded 180 degrees creating therefore a pulling tab, and enabling the user to expose the powders by pulling away the cover sheet from the base sheet. The active pharmaceutical ingredients packed in the blisters of said strip may be used as such or they may be combined with suitable excipients. The term medicament therefore, used throughout the present description and claims, designates either the pharmaceutical ingredient as such or its combination with suitable excipients.

Another aspect of the present invention is the mouthpiece of the aforementioned device. Said mouthpiece enables the simultaneous release of the powders comprised in both blisters by a single inhalation. Furthermore, it enables the adjustment of the inhaler's resistance by simple means during its manufacture. The resistance of a dry powder inhaler corresponds to the force by which the patient has to inhale in order to receive the medicament. It is desirable that the resistance of the device is not very high so that the device may be used by a wide variety of patients. Furthermore, with the present invention there is no powder accumulation in the interior walls of the mouthpiece, something very important for the efficacy and safety of the inhaler.

The mouthpiece comprises three main parts, the first being the exterior part, i.e. the one that the patient places in his mouth during the inhalation, and two interior parts, the first of which is fixed on top of the other. The upper part is generally of conical shape, and its top constitutes the exit of the powder from the device, whereas its base is fixed at the top of the lower part of the mouthpiece. Said lower part comprises at least one opening which serves as the entrance of the inhaled air into it and two pairs of two openings at its base, said base being the base of the mouthpiece which touches the strip while at the same time covering completely the powder containing blisters. The first opening of each pair represents the entrance of the air into each blister and the second opening represents the exit of the powder from each blister respectively. Each of the powder exit openings constitutes also the base of a cylinder, which is positioned in a generally vertical orientation with regard to the base of the mouthpiece, the height of said cylinders being at least equal to the height of the lower part of the mouthpiece. The two cylinders may have the same or different heights and the same or different diameters, depending on the properties of each powder. It is generally preferred that the height of each cylinder is such that its top does not exceed 50% of the height of the upper part of the mouthpiece. It is particularly preferred that the top of each cylinder does not exceed 20% of the height of the upper part of the mouthpiece, and it is even more particularly preferred that it does not exceed 10% of said height. The top of the lower part of the mouthpiece is sealed by a cover which bears two openings through which the two cylinders pass. According to the present invention the size of each opening is larger than the diameter of the corresponding cylinder. The gaps between the openings of the cover and each cylinder respectively allow for a portion of the air which enters the lower part of the mouthpiece instead of heading towards the powder containing blisters, to pass through said gaps and to exit the mouthpiece through its upper part. In this manner the resistance of the device is reduced since the pressure which is created within the air which enters the lower part of the mouthpiece is released when part of the air passes through said gaps. Hence, the amount of air which passes into the upper part of the mouthpiece in a unit of time is increased and therefore the resistance of the device is reduced. The resistance can be easily modified by changing the size of the openings of the cover, while the remaining parts of the mouthpiece remain unchanged, which means that the device of the present invention can be manufactured and modified in a cost effective and simple manner. According to the present invention, the two gaps may have the same or different sizes. The size of the gaps depends on the properties of each powder and on the group of patients that use the device. It is generally preferred that the overall surface of the gaps should be up to three times greater than the surface of the opening(s) for the entrance of the air into the lower part of the mouthpiece. It is more preferred that the surface of the gaps should be up to two times greater than the surface of the air opening(s), and it is particularly preferred that it should be up to one and a half times greater than the surface of the air opening(s) for the entrance of the air into the lower part of the mouthpiece.

With the mouthpiece of the present invention no accumulation of powder on the inner walls of the inhalation device is observed. This feature is very important for the efficacy of the device since it ensures that the patient inhales every time the required dose of the medicament.

The inhalation device of the present invention is used in the following way: The user lifts the mouthpiece from its basic position and places a blister strip on the support surface in such a way that the attachment formation of the strip is combined with the corresponding attachment point of the surface. The strip is aligned with the help of the guides and the blisters enter the cavities of the surface. Then, the user returns the mouthpiece to its basic position and exposes the powder by pulling away the cover sheet of the strip. At this point the base of the mouthpiece touches the strip while it covers completely the powder containing blisters and the device is ready for inhalation. The user then inhales the powder and by lifting the mouthpiece from its basic position in order to replace the used strip, he verifies that he has inhaled the entire amount of the powder.

The present invention exhibits significant advantages compared to the state of the art. Since the two pharmaceutical compounds do not come into contact prior to the inhalation process but only after they leave the cylinders of the mouthpiece, they do not interact with each other and therefore the possibility of decomposition as a result of such interaction is eliminated. This means that the device of the present invention provides for the possibility of simultaneous administration of a far greater number of medicament combinations since it allows the simultaneous administration of medicaments which are chemically incompatible with each other. Additionally, since each pharmaceutical compound is situated in a different blister, it is possible to develop two different pharmaceutical compositions, so that the end product contains the best possible composition for each active ingredient. Hence the development of the products becomes far easier and cost effective, since there is no need to develop a pharmaceutical composition which is suitable for both active ingredients at the same time.

The drawings that follow illustrate some examples of the present invention.

DETAILED DESCRIPTION OF THE DRAWINGS

Figure 1:
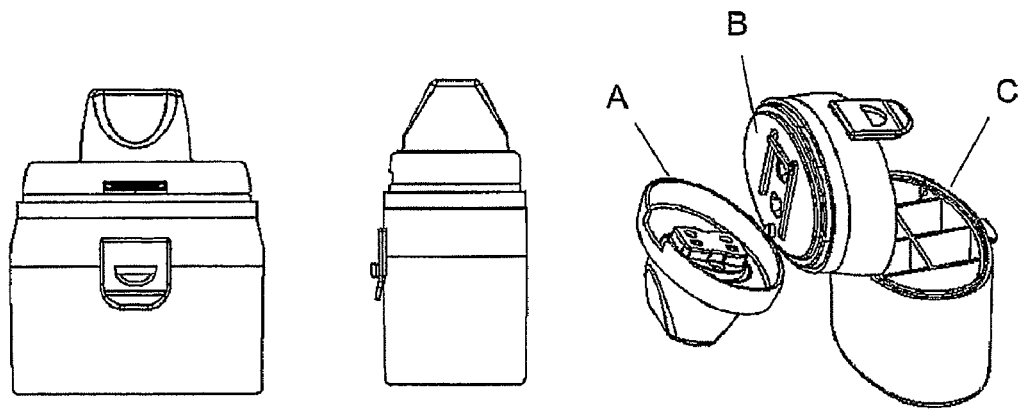
FIG. 1 shows an inhalation device according to the present invention.

FIG. 1 shows an example of a dry powder inhalation device suitable for the simultaneous administration of more than one pharmaceutical compounds wherein the powder is packed in the blisters of single dose blister strips, and wherein said device comprises a mouthpiece (A), a blister strip support surface (B) and a strip storage compartment (C).

Figure 2:
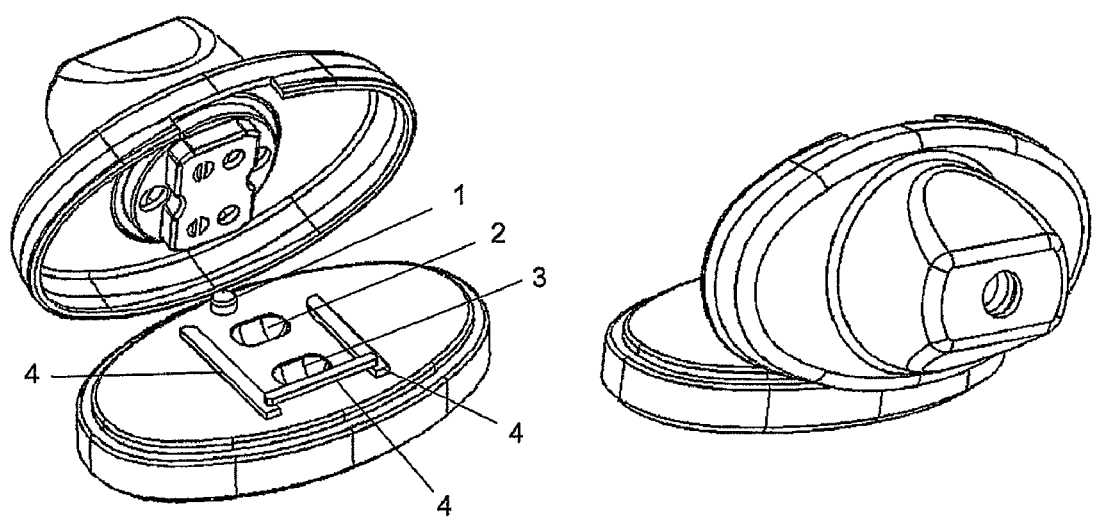
FIG. 2 shows the blister strip support surface of the inhalation device.

The blister strip support surface (B) (FIG. 2) comprises a protrusion (1) which serves as an attachment point, two cavities (2) and (3), which accommodate the blisters of the strip, and guides (4) for the correct alignment and firm placement of the strip. The mouthpiece (A) is movably joined to the support surface (B). In order to allow for the placement of the strip in the device, the mouthpiece (A) is lifted from its basic position.

Figure 3:
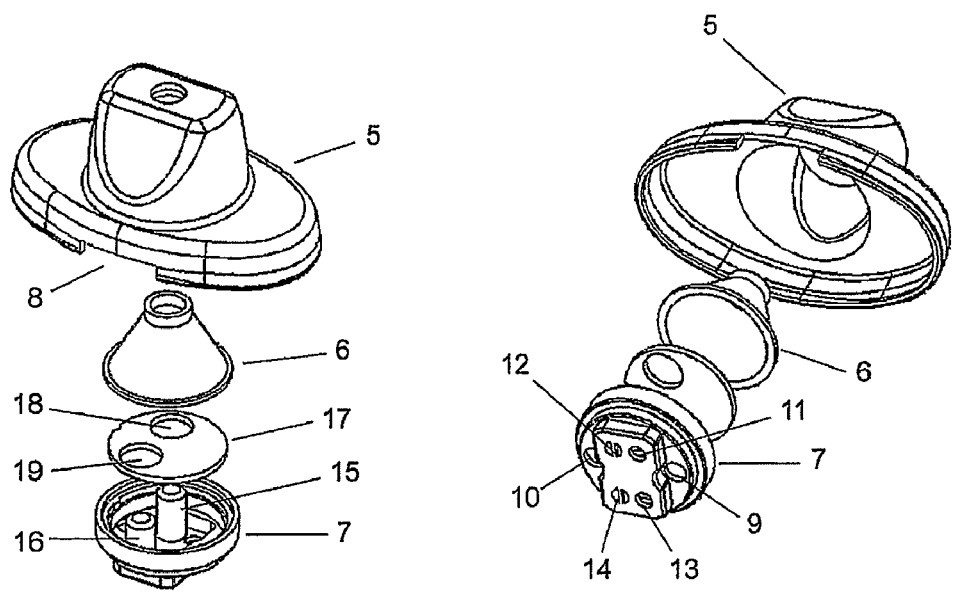
FIG. 3 shows the mouthpiece of the device.
Figure 4:
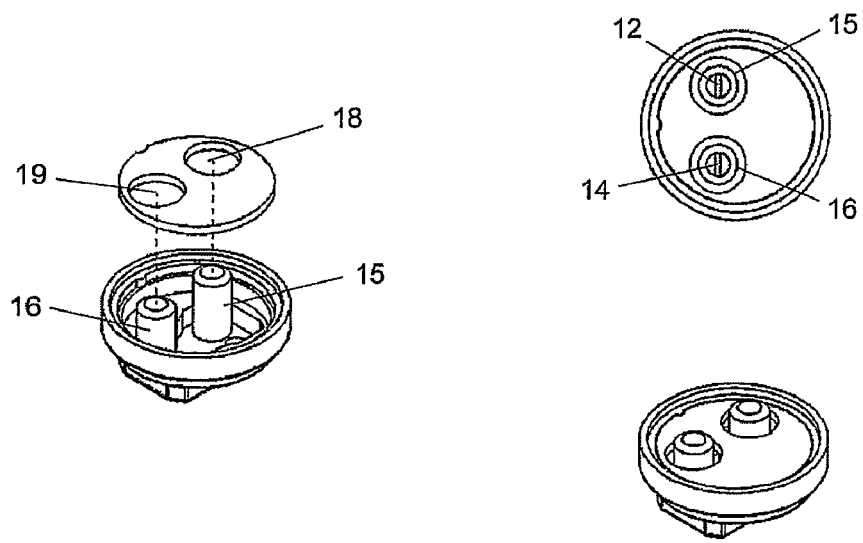
FIG. 4 shows the lower part of the mouthpiece of the device.

FIG. 3 shows an example of a mouthpiece according to the present invention. The mouthpiece comprises three main parts: The external part (5), which the patient places in his mouth during the inhalation, and two internal parts (6 and 7). The external part (5) comprises an opening (8) for the entrance of the air into the device. The upper internal part (6) is generally of conical shape and is accommodated at the inner walls of the external part (5). The top of the cone (6) represents the exit of the powder from the device, whilst its base is fitted to the top of the lower part (7). The latter part comprises two openings (9 and 10) for the entrance of the air into it, and two pairs of two openings (11, 12 and 13, 14) at its base. Two of the openings (11 and 13) constitute the entrance of the air into each powder containing blister and the other two openings (12 and 14) the exit of the powder from each of the blisters. The openings for the exit of the powder (12 and 14) bear a sieve, which is optional according to the invention, and which prevents the particles that are larger than the desired size to pass through the mouthpiece. These openings (12 and 14) represent also the bases of two cylinders (15 and 16) whose height is slightly larger than that of the lower part (7). The top of the lower part (7) is sealed by a cover (17) which bears two openings (18 and 19) through which the two cylinders (15 and 16) pass. As it is clearly depicted in FIG. 4, the size of each opening (18 and 19) is larger than the diameter of the respective cylinder (15 and 16) and in this way two gaps are formed through which a portion of the air that enters the lower part (7) passes, as it is explained herein below.

Figure 5:
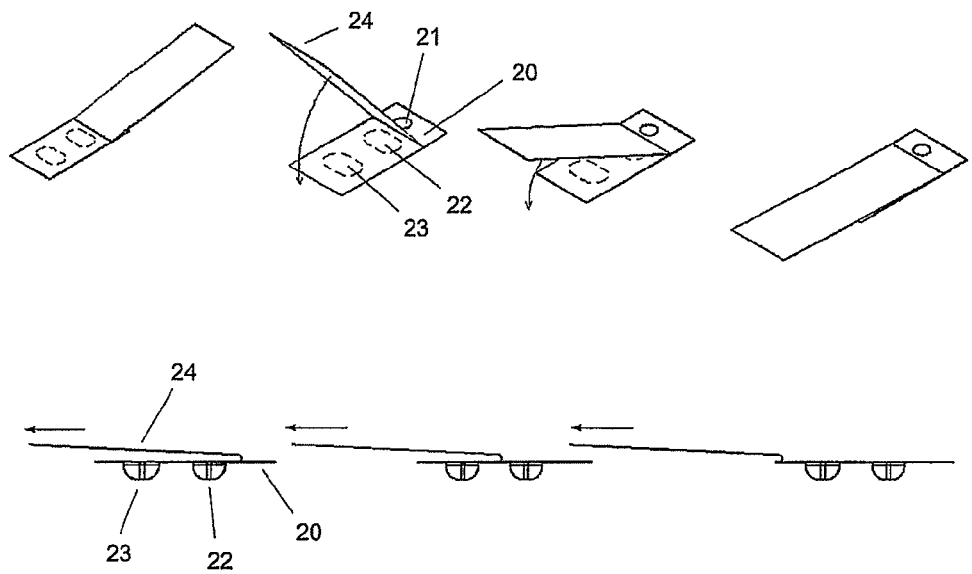
FIG. 5 shows a single dose blister strip according to the present invention.

The single dose blister strip (FIG. 5) comprises a base sheet (20) and a cover sheet (24). The base sheet (20) comprises an attachment formation (in the specific example a hole (21)) and two blisters (22 and 23), each of which contains a different pharmaceutical compound. The base sheet (20) is sealed by the cover sheet (24) in the area around the blisters (22 and 23). The free end of the cover sheet, which initially covers the hole (21), is then folded by 180 degrees creating therefore a pulling tab and enabling the user to expose the powders by pulling away the cover sheet (24) from the base sheet (20).

Figure 6:
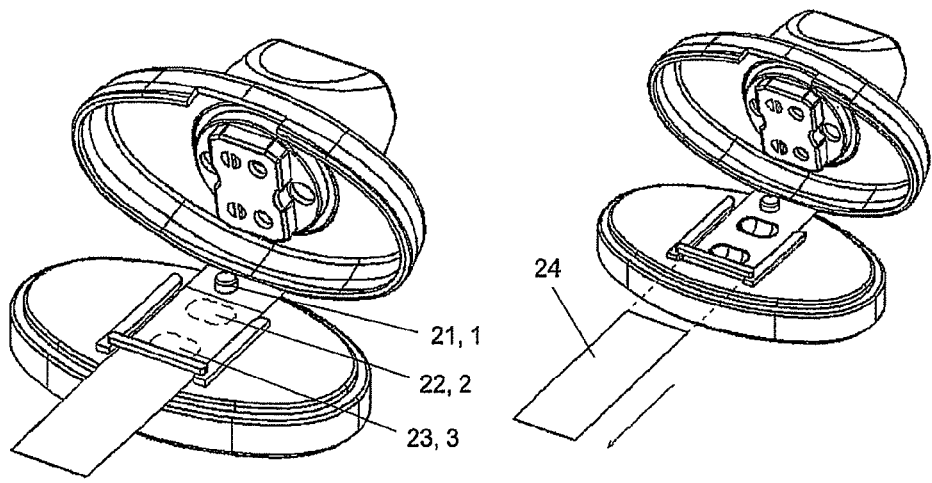
FIG. 6 shows the manner by which the blister strip is placed in the device.

FIG. 6 show the manner by which the single dose blister strip is placed in the inhalation device. Thus, after the mouthpiece has been lifted from its basic position, the hole (21) of the strip is passed through the protrusion (1) of the support surface and each of the blisters (22 and 23) enters the corresponding cavity (2 and 3). Then the user returns the mouthpiece to its basic position and pulls the cover sheet (24) until it is detached from the base sheet (20). In case that the user so wishes, he can lift the mouthpiece from its basic position in order to verify that the powder is available for inhalation.

Finally, and while the mouthpiece is at its basic position, the user inhales the powder and then, by lifting the mouthpiece in order to replace the used strip, he can check that he has inhaled the entire dose of the medicaments.

Figure 7:
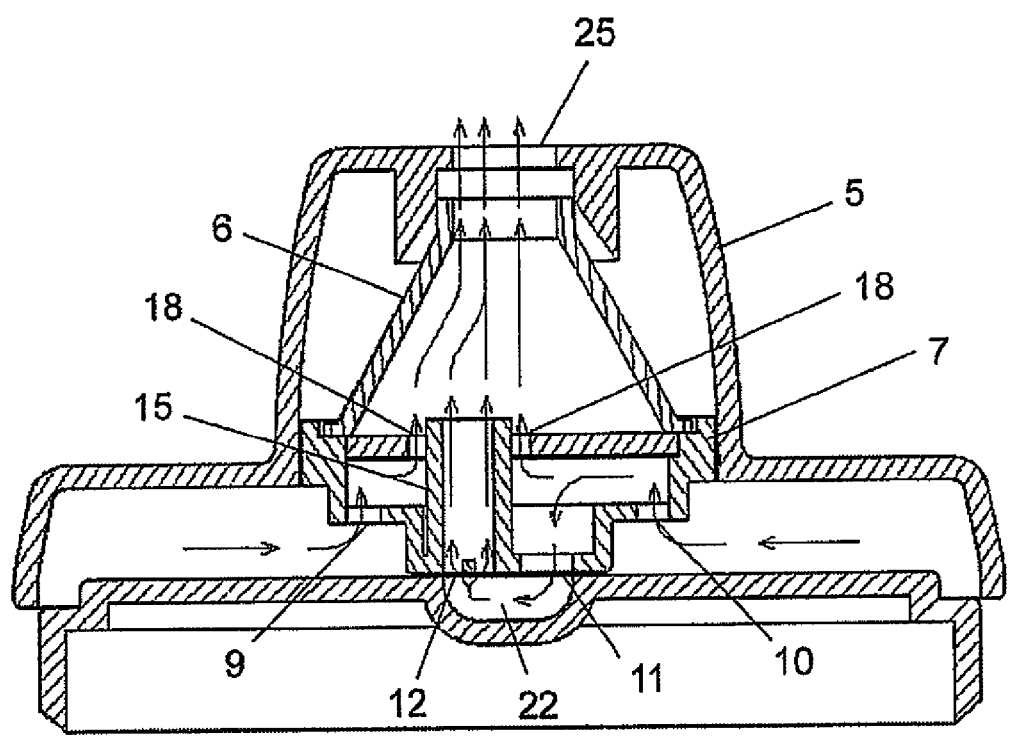
FIG. 7 shows a vertical section of the mouthpiece and the air flow through it.

FIG. 7 shows a vertical section of the mouthpiece of FIG. 3 and the air flow through it. For visibility reasons only one of the cylinders and the pair of openings that cover one of the blisters is shown, whereas what is mentioned below can be equally applied to the second cylinder and the pair of openings that cover the second blister.

The air enters the mouthpiece through one or more openings that are not shown in this specific drawing. Then, through (in this specific example) two openings (9 and 10) the air enters the lower part (7) of the mouthpiece. There, a portion of the air passes through the opening (11) for the entrance of the air into the blister (22), carries away the powder situated in the blister (22) of the strip, and the mixture of air and powder passes through the opening (12) for the exit of the powder from the blister into the cylinder (15) and enters the upper part (6) of the mouthpiece. A second portion of the air that enters the lower part (7), passes through the opening (18) and enters the upper part (6). This air meets the mixture of air and powder that exits the cylinder (15) and is combined with them, creating a new mixture of air and powder which exits the mouthpiece through the opening (25). In the same way, the air that enters the lower part (7) carries away the powder situated in the second blister (23), while a portion of it passes through the opening (19) (not shown). Hence, the powders situated in the two blisters (22 and 23) come into contact with each other for the first time in the upper part (6) of the mouthpiece, just before they exit the device. The present invention therefore ensures the simultaneous administration of a combination of pharmaceutical compounds, while avoiding the disadvantages of the prior art.

The invention claimed is:

1. A combination of a dry powder inhalation device and a single dose blister strip for the simultaneous administration of two medicaments wherein the device comprises a mouthpiece (A), a strip support surface (B) and a strip storage compartment (C), wherein the strip support surface comprises an attachment point (1), a cavity (2) which receives a powder containing blister (22), and guides (4), wherein the mouthpiece (A) is movably joined to the strip support surface (B) so as when the device is ready for inhalation the base of the mouthpiece (A) touches the strip and covers completely the powder containing blister (22), and wherein the single dose blister strip comprises a base sheet (20) and a cover sheet (24), wherein the base sheet (20) comprises an attachment formation (21) and a blister (22), wherein the cover sheet seals the base sheet (20) so as it can be detached by pulling away from the base sheet (20), wherein said mouthpiece (A) comprises an upper part (6) and a lower part (7), wherein the lower part (7) comprises at least one opening (9,10) for the entrance of the air into it and whose base comprises two openings (11,13) for the entrance of the air into each blister (22,23), and two openings (12,14) for the exit of the powder from each blister (22,23) wherein each opening (12,14) for the exit of the powder from the blister (22,23) constitutes the base of two cylinders (15,16) whose height is at least equal to the height of the lower part of the mouthpiece (7) and wherein the top of said part (7) is sealed by a cover (17) which bears two openings (18,19) through which the two cylinders (15, 16) pass and wherein the size of each opening (18,19) is larger than the diameter of the corresponding cylinders (15,16), and wherein the strip support surface (B) further comprises a second cavity (3) which receives a second powder containing blister (23), the base sheet (20) of the strip further comprises a second blister (23) which contains a medicament other than the one contained in the first blister (22) and when the device is ready for inhalation the base of the mouthpiece (A) further covers the second blister (23) completely.

2. A combination according to claim 1, wherein the attachment point is a protrusion (1) and the attachment formation is a hole (21).

3. A combination according to claim 1, wherein the overall surface of the gaps between the openings (18, 19) of the cover (17) and the two cylinders (15, 16) is up to three times greater than the surface of the air opening(s) (9, 10) for the entrance of the air into the lower part (7) of the mouthpiece.

4. A combination according to claim 3, wherein the surface of the gaps is up to two times greater.

5. A combination according to claim 4, wherein the surface of the gaps is up to one and a half times greater.

6. A combination according to any of claim 1, wherein the height of each cylinder (15, 16) is such that its top does not exceed 50% of the height of the upper part (6) of the mouthpiece.

7. A combination according to claim 6, wherein the top of each cylinder (15, 16) does not exceed 20% of the height of the upper part (6) of the mouthpiece.

8. A combination according to claim 7, wherein the top of each cylinder (15, 16) does not exceed 10% of the height of the upper part (6) of the mouthpiece.

9. A combination as claimed in claim 2, wherein the overall surface of the gaps between the openings (18, 19) of the cover (17) and the cylinders (15,16) is up to three times greater than the surface of the air openings (9,10) for the entrance of the air into lower part (7) of the mouthpiece.

10. A combination according to claim 9, wherein the height of each cylinder (15, 16) is such that its top does not exceed 50% of the height of the upper part (6) of the mouthpiece.

11. A combination according to claim 2, wherein the height of each cylinder (15, 16) is such that its top does not exceed 50% of the height of the upper part (6) of the mouthpiece.

12. A combination according to claim 3, wherein the height of each cylinder (15, 16) is such that its top does not exceed 50% of the height of the upper part (6) of the mouthpiece.

13. A combination according to claim 4, wherein the height of each cylinder (15, 16) is such that its top does not exceed 50% of the height of the upper part (6) of the mouthpiece.

* * * * *